United States Patent [19]

Milligan

[11] 4,134,854
[45] * Jan. 16, 1979

[54] NONIONIC SURFACTANT WITH LOW POUR POINT

[75] Inventor: John G. Milligan, Austin, Tex.

[73] Assignee: Texaco Development Corp., New York, N.Y.

[*] Notice: The portion of the term of this patent subsequent to Aug. 14, 1990, has been disclaimed.

[21] Appl. No.: 593,359

[22] Filed: Jul. 7, 1975

Related U.S. Application Data

[63] Continuation-in-part of Ser. No. 356,824, May 5, 1973, abandoned, which is a continuation-in-part of Ser. No. 32,423, Apr. 27, 1970, Pat. No. 3,752,857, which is a continuation-in-part of Ser. No. 790,445, Jan. 10, 1969, abandoned, which is a continuation-in-part of Ser. No. 671,995, Oct. 2, 1967, abandoned.

[51] Int. Cl.$^2$ .............................................. B01F 17/00
[52] U.S. Cl. .............................. 252/351; 252/DIG. 1; 568/625
[58] Field of Search ......................... 252/351, DIG. 1; 260/615 B

[56] References Cited

U.S. PATENT DOCUMENTS

| | | | |
|---|---|---|---|
| 3,030,426 | 4/1962 | Moseley | 260/615 B |
| 3,324,035 | 6/1967 | Nankee et al. | 260/615 B |
| 3,340,309 | 9/1967 | Weipeit | 260/615 B |
| 3,567,784 | 3/1971 | Tsatsos et al. | 260/615 B |
| 3,752,857 | 8/1973 | Milligan | 260/615 B |

FOREIGN PATENT DOCUMENTS 950844  2/1964  United Kingdom .................. 260/615 B

*Primary Examiner*—Leland A. Sebastian
*Assistant Examiner*—J. L. Barr
*Attorney, Agent, or Firm*—Carl G. Ries; Thomas H. Whaley; James L. Bailey

[57] ABSTRACT

Nonionic surface-active agents prepared by the addition of ethylene oxide to mixtures of alcohols containing from 8 to 20 carbon atoms are often solids or mixtures of solids and liquids at room temperatures. The pour points of such nonionic surfactants can be lowered without appreciably adversely affecting other properties by the sequential addition of ethylene oxide, propylene oxide and ethylene oxide to the alcohol if the initial oxyethylene block contains from 30% to 60% of the total oxyethylene groups in the molecule.

2 Claims, No Drawings

NONIONIC SURFACTANT WITH LOW POUR POINT

CROSS-REFERENCE TO RELATED APPLICATION

This is a continuation-in-part of copending application Ser. No. 356,824 filed May 5, 1973 now abandoned, which is a continuation-in-part of application Ser. No. 32,423, filed Apr. 27, 1970 now U.S. Pat. No. 3,752,857, which is a continuation-in-part of copending application Ser. No. 790,445, filed Jan. 10, 1969, now abandoned, which is a continuation-in-part of application Ser. No. 671,995, filed Oct. 2, 1967, now abandoned. The contents of said applications Ser. Nos. 356,824; 32,423; 790,445 and 671,995 are hereby incorporated herein by reference thereto.

BACKGROUND OF THE INVENTION

This invention is concerned with nonionic surface-active agents prepared from mixtures of alcohols containing from 8 to 20 carbon atoms by the sequential addition of ethylene oxide, propylene oxide and ethylene oxide. Such surfactants have lower pour points than straight ethylene oxide adducts having corresponding cloud points. Surface properties are not appreciably affected.

It has long been the practice to prepare surface-active agents by the addition of ethylene oxide to long chain alcohols. It is also well known to prepare mixed adducts of ethylene oxide and propylene oxide. Adducts containing a random distribution of oxyethylene and oxypropylene groups and adducts containing discreet blocks of polyoxyethylene and polyoxypropylene chains have been prepared. The straight ethylene oxide adducts often contain solids, making them difficult to handle at temperatures ordinarily encountered. The use of premixed ethylene oxide and propylene oxide results in a surfactant product having a lower pour point; but the product is not entirely satisfactory in that it may contain solids; may not be satisfactorily biodegradable, etc.

SUMMARY OF THE INVENTION

I have now discovered a class of surface-active agents having lower pour points but whose cloud points and surface properties have not been adversely affected. The nonionic surface-active agent of my invention is a mixture of compounds having the formula:

$$R-(OCH_2CH_2)_n-(OCH_2CH)_p-(OCH_2CH_2)_m-OH$$
$$\qquad\qquad\qquad\qquad\quad\ \ |$$
$$\qquad\qquad\qquad\qquad\quad CH_3$$

wherein R is a $C_8$-$C_{20}$ straight or branched alkyl group, n and m are from 2 to 10 and are chosen such that $n/n+m$ is within the range of 0.2 to 0.6 and p is 0.5 to 3 such that $p/n+m$ is within the range of 0.119 to 0.25. Preferably, $n/n+m$ is 0.3 to 0.5.

DESCRIPTION OF THE PREFERRED EMBODIMENT

The surface-active agents of my invention are prepared by the sequential addition of ethylene oxide, propylene oxide and more ethylene oxide to a mixture of alcohols containing from 8 to 20 carbon atoms. The addition of alkylene oxides to alcohols is a well known reaction. It may be conducted in the presence of either acidic or alkaline catalysts with the latter being preferred. Examples of typical acidic catalysts include sulfuric acid, phosphoric acid and Lewis acids such as stannic chloride and boron trifluoride. Typical alkaline catalysts include tertiary amines, sodium hydroxide, potassium hydroxide, quaternary ammonium hydroxides, sodium carbonate, potassium carbonate, sodium methoxide, calcium hydroxide and barium hydroxide. The especially preferred catalysts are sodium hydroxide and potassium hydroxide.

The addition of alkylene oxides to alcohols proceeds readily at temperatures within the range of 50° to 200° C. Since both ethylene oxide and propylene oxide are gases at this temperature, the reaction is preferably conducted in a closed vessel under pressure. The particular pressure employed is not critical and autogenous pressures are generally used.

Initially, from 20% to 60% of the total ethylene oxide should be added to the alcohol. Preferably 30% to 50% of the ethylene oxide is added initially. The addition of this block of ethylene oxide is followed by a block of propylene oxide. The remainder of the ethylene oxide is then added.

A total of from about 6 to about 40 mols of ethylene oxide may be employed. The amount of ethylene oxide used is based upon the desired cloud point. Higher cloud points require more ethylene oxide. The amount of propylene oxide may be virtually any amount such that the molar ratio of propylene oxide to ethylene oxide is at least 0.1. Preferably, this ratio will be from about 0.119 to about 0.25. Amounts of propylene oxide in excess of this show no appreciable benefit, and from a practical standpoint propylene oxide in excess of that required to give a molar ratio of propylene oxide (PO) to ethylene oxide (EO) of 0.9 will not be employed.

My invention will be further illustrated by the following examples:

EXAMPLE I

A series of adducts of a commercial mixture of straight chain alcohols containing 12, 14, 16 and 18 carbon atoms was prepared. The alcohol mixture used is trademarked Alfol 1218 by the Continental Oil Company. The mixture is comprised of about 40% $C_{12}$, 30% $C_{14}$, 20% $C_{16}$ and 10% $C_{18}$ primary normal alcohols. The alcohol was mixed with 0.6% of its weight of potassium hydroxide and the oxides were added sequentially at 140° C. under an atmosphere of nitrogen. The final ethylene oxide block was added until a cloud point of 88° to 90° C. was reached. An adduct of this alcohol mixture made with only ethylene oxide to a cloud point of 90° C. is a solid at room temperature. The position of the polyoxypropylene block within the polyoxyalkylene chain was varied by varying the percentage of ethylene oxide added in the first block. For comparison, an adduct was also prepared using premixed oxides. The results are summarized in Table 1.

TABLE 1

| | | Structured by Mols | | | | | |
|---|---|---|---|---|---|---|---|
| Run | Alcohol | EO | PO | EO | Ratio PO/EO | Cloud Point, °C | Pour Point, °C |
| 1 | 1 | 4.4 | 1.91 | 9.93 | .133 | 89 | 13 |
| 2 | 1 | 5.4 | 1.91 | 9.32 | .13 | 89.5 | 6.5 |
| 3 | 1 | 6.4 | 1.91 | 8.9 | .134 | 89.5 | 6 |
| 4 | 1 | 7.4 | 1.91 | 7.9 | .125 | 88 | 9 |
| 5 | 1 | 7.78 | 1.92 | 8.3 | .119 | 90 | 13 |
| 6 | 1 | 8.4 | 1.91 | 6.9 | .119 | 88.5 | 11 |
| 7 | 1 | 9.4 | 1.91 | 6.5 | .12 | 88 | 12.5 |
| 8 | 1 | 15.3 | 1.91 | 3.7 | .1 | 89 | 25.5 |
| 9 | 1 | 15.3 | 1.9 | (pre | .124 | 89 | 24 |

TABLE 1-continued

| Run | Alcohol | EO | PO | EO (mixed) | Ratio PO/EO | Cloud Point, °C | Pour Point, °C |
|-----|---------|----|----|------------|-------------|-----------------|----------------|

It can be seen from the table that those adducts containing from 30% to 60% of the ethylene oxide in the initial block have pour points of 13° C. or below. In the last two runs wherein this ratio was not maintained, the pour points were significantly higher. For example, a solid product was obtained when straight ethylene oxide was used. A pour point of 25.5° C. resulted when 80% of the ethylene oxide is in the initial block (Run 8) and a pour point of 24° C. when the oxides are premixed (Run 9).

To demostrate that the amount of propylene oxide added is not particularly critical to the invention, a series of runs was made in which the amount of propylene oxide added was varied. The alcohol employed was a commercially available mixture of 12 and 13 carbon straight and branched alcohols. The alcohol mixture used is trademarked Neodol 23 by Shell Chemical Company. It is a mixture of primary alcohols with about 40% $C_{12}$ alcohols and 60% $C_{13}$ alcohols, mainly normal with not more than about 26% branched isomers. The branched isomers are mostly 2-methyl substituted. The alcohols are prepared by the oxo process from straight chain olefins. In all runs, 50% of the ethylene oxide was added in the initial block. The amount of ethylene oxide employed was varied slightly from run to run to keep the cloud point essentially constant. The results are summarized in Table 2. Wetting times are included to give a comparison of surface properties of the adducts. The Draves wetting time method is reported in the 1967 Edition of the Technical Manual of the American Association of Textile Chemist and Colorists, Vol 43, September, 1967. As shown in the Manual, the properties of a liquid medium are modified by admixing an effective amount of a compound of this invention in the liquid medium. The principle of the Draves test is shown by dropping a weighted cotton test skein into a tall cylinder containing a water solution of the wetting agent of this invention. The time required for a string stirrup connecting the weight and skein to relax is recorded as the sinking time. Shorter times indicate a more effective wetting time.

TABLE 2

| Run No. | 1 | 2 | 3 | 4 | 5 |
|---------|---|---|---|---|---|
| Ethylene oxide, mols | 7 | 8 | 8 | 9 | 9 |
| Propylene oxide, mols | 0 | 1.5 | 2.0 | 3.0 | 4.0 |
| Ratio PO/EO | — | 0.1875 | 0.25 | 0.33 | 0.44 |
| Cloud point, °C | 53 | 57 | 54 | 56 | 52 |
| Freezing point, °C | 17 | −6 | −6 | −6 | −6 |
| Wetting times, Draves 1.5 g. hook at 25° C | | | | | |
| 0.25 wt. % | 2.9 | 3.6 | 3.3 | 3.2 | 3.9 |
| 0.10 wt. % | 10.5 | 10.3 | 10.4 | 11.7 | 11.3 |
| Ratios of PO/EO such as in the range of about 0.1875 to 0.25 are demonstratively shown to be effective. | | | | | |
| 3.0 g. hook at 25° C | | | | | |
| 0.10 wt. % | 6.6 | 5.9 | 5.5 | 6.7 | 5.3 |
| 0.05 wt. % | 15.8 | 15.4 | 17.8 | 16.2 | 15.1 |

As can be seen from Table 2, the insertion of a block of oxypropylene groups in the center of the polyoxyalkylene chain resulted in a lowering of the freezing point by 23° C. without appreciably affecting the cloud point and wetting properties of the surfactant. The use of from 1.5 to 4 mols of propylene oxide did not appreciably change the properties of the adduct.

The surfactants of my invention (Compounds C and D) are compared with compounds prepared from n-butanol and n-hexanol in Table 3. The compound prepared from n-butanol is found in Nankee's U.S. Pat. No. 3,324,035 (1967). The compounds prepared from n-butanol and n-hexanol (Compounds A and B) are not surfactants as shown by their poor wetting and foaming properties in Table 3.

The four compounds of Table 3 were tested for detergency in a Terg-O-Tometer. See J. C. Harris, Detergency Evaluation and Testing, Interscience Publishers, Inc., New York, 87–90 (1954). For the Terg-O-Tometer test, a piece of U.S. Testing Company standard soiled cotton cloth (reflectance 23) and a standard Testfabrics, Inc. soiled cotton cloth (reflectance 25) were washed in a liter of warm water containing 150 parts per million (ppm.) hardness and 1.67 g. $K_4P_2O_7$, 0.50 g. $K_2CO_3$, 0.05 g. carboxymethyl cellulose and a surfactant of my invention or a compound prepared from n-butanol or n-hexanol. The wash time was 15 minutes and the wash was followed by two 5-minute warm rinses with one liter of water of each rinse. The washed cloths were ironed dry and the reflectances were measured on a modified Photovolt photometer with a green tristimulus filter. The reflectances are shown as the percent of the reflectance of magnesium oxide. This system is useful for measuring the amount of soil removed from cloth.

The Ross Miles Foam Height test gives the height of the foam generated on dropping 0.1% solution of the surfactant into more of the solution at 120° F. both initially and after standing five minutes. The Foam Height test is reported by John Ross and G. D. Miles in *Oil and Soap*, 18, 99–102 (1941).

The chemical structures of the compounds in Table 3 are as follows:

TABLE 3

| Compound | Structure By Mols Alcohol | EO | PO | EO | Ratio PO/EO |
|----------|---------------------------|-----|-----|-----|-------------|
| A | n-Butanol | 3.4 | 0.5 | 0.5 | 0.13 |
| B | n-Hexanol | 2 | 1 | 2 | 0.25 |
| C | Mixture of 12, 14, 16 & 18 Carbon Atoms | 7.78 | 1.92 | 8.3 | 0.119 |
| D | Mixture of 12 & 13 Carbon Atoms | 4 | 1.5 | 4 | 0.19 |

| Compound | None | A | B | C | D |
|----------|------|---|---|---|---|
| Skein wetting at 25° C | | | | | |
| 3 g. Hook, 0.25%, seconds | — | >120 | >120 | 52.4 | — |
| 3 g. Hook, 0.1%, seconds | — | >120 | >120 | 45.1 | 5.9 |
| Ross Miles foam height at 120° F | | | | | |
| Initial, mm. | — | 15 | <1 | 110 | 57 |

-continued

| Compound | None | A | B | C | D |
|---|---|---|---|---|---|
| After 5 minutes, mm. | — | 4 | <1 | 7 | 10 |
| Terg-O-Tometer, reflectance at 0.2% concentration | | | | | |
| U.S. Testing Co. cloth | 30 | 30 | 30 | 39 | 45 |
| Testfabrics, Inc. cloth at 0.1% concentration | 39 | 39 | 40 | 44 | 48 |
| U.S. Testing Co. cloth | 30 | 29 | 31 | 39 | 43 |
| Testfabrics, Inc. cloth | 39 | 37 | 40 | 43 | 63 |
| Cloud point, 1% aqueous solution, °C | — | >93 | 68 | 90 | 57 |

The data in Table 3 illustrate that Compounds A and B, which are prepared from n-butanol and n-hexanol, respectively, did not wash any better than the blank of the first column whereas Compounds C and D of my invention showed superior wash properties. While Compounds C and D showed good wetting and foaming properties, Compounds A and B showed poor wetting and foaming properties. The higher reflectances for Compounds C and D of my invention show a cleaner cloth than the reflectances for Compounds A and B which show essentially no improvements over the blank. Thus, the data of Table 3 illustrate that compounds of my invention are surfactants while compounds prepared from lower alcohols are not surfactants.

While the invention has been explained in relation to its preferred embodiment, it is to be understood that various modifications thereof will become apparent to those skilled in the art upon reading the specification and is intended to cover such modifications as fall within the scope of the appended claims.

I claim:

1. A surfactant which is a mixture of compounds having the formula:

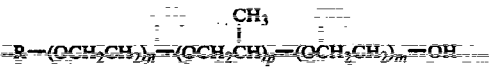

wherein R is a straight or branched alkyl group from 8 to 20 carbon atoms, n and m are from 2 to 10 and are chosen such that $n/n+m$ is within the range of 0.2 to 0.6 and p is 0.5 to 3 such that $p/n+m$ is within the range of about 0.119 to 0.25.

2. A surfactant as in claim 1 wherein $n/n+m$ is within the range of 0.3 to 0.5